United States Patent
Hell

(10) Patent No.: US 9,377,406 B2
(45) Date of Patent: Jun. 28, 2016

(54) METHOD OF SPATIAL HIGH RESOLUTION IMAGING OF A STRUCTURE OF A SAMPLE, THE STRUCTURE COMPRISING A LUMINOPHORE

(71) Applicant: Max-Planck-Gesellschaft zur Foerderung der Wissenschaften e.V., Munich (DE)

(72) Inventor: Stefan W. Hell, Goettingen (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 14/791,919

(22) Filed: Jul. 6, 2015

(65) Prior Publication Data
US 2015/0308954 A1 Oct. 29, 2015

Related U.S. Application Data

(63) Continuation of application No. PCT/EP2014/050270, filed on Jan. 9, 2014.

(30) Foreign Application Priority Data

Jan. 9, 2014 (DE) .................. 10 2013 100 174

(51) Int. Cl.
*G01T 1/00* (2006.01)
*G01N 21/64* (2006.01)
(Continued)

(52) U.S. Cl.
CPC ............ *G01N 21/64* (2013.01); *G01N 21/1717* (2013.01); *G01N 21/6458* (2013.01);
(Continued)

(58) Field of Classification Search
CPC ............................. G01N 21/64; G01N 21/65
USPC ........................................................ 250/484.4
See application file for complete search history.

(56) References Cited

U.S. PATENT DOCUMENTS

| | | | |
|---|---|---|---|
| 7,224,452 B2 | 5/2007 | Hell | |
| 8,399,857 B2 | 3/2013 | Lippert | |

FOREIGN PATENT DOCUMENTS

| | | |
|---|---|---|
| DE | 10 2006 046 369 A1 | 4/2008 |
| EP | 1 582 858 A1 | 10/2005 |

OTHER PUBLICATIONS

Grotjohann et al. "Diffraction-unlimited all-optical imaging and writing with a photochromic GFP", Nature vol. 478, Oct. 13, 2011, pp. 204-208.*

(Continued)

*Primary Examiner* — David Porta
*Assistant Examiner* — Meenakshi Sahu
(74) *Attorney, Agent, or Firm* — Thomas | Horstemeyer, LLP

(57) ABSTRACT

For spatial high resolution imaging of a structure of a sample, the structure comprising a luminophore, the sample, in a measurement area, is subjected to an intensity distribution of luminescence inhibiting light comprising a local minimum. Then, the sample, in the measurement area, is subjected to luminescence excitation light which excites the luminophore out of an electronic ground state into a luminescent state, and luminescence light emitted out of the measurement area is registered. This registered luminescence light is assigned to the position of the local minimum within the sample. The luminescence inhibiting light disturbs the electronic ground state of the luminophore such that the luminophore, in the disturbed electronic ground state, has an absorption cross-section for the luminescence excitation light which is reduced by at least 50% as compared to the undisturbed electronic ground state.

20 Claims, 4 Drawing Sheets

(51) Int. Cl.
   *G01N 21/17* (2006.01)
   *G01N 21/65* (2006.01)
(52) U.S. Cl.
   CPC ........ *G01N21/65* (2013.01); *G01N 2021/1731* (2013.01); *G01N 2021/6439* (2013.01); *G01N 2201/061* (2013.01)

(56) References Cited

OTHER PUBLICATIONS

PCT International Preliminary Report in co-pending, related PCT Application No. PCT/EP2014/050270, mailed Jul. 14, 2015.

Andresen M. et al.: "Structure and Mechanism of the reversible photoswitch of a fluorescent protein", Proceedings of the National Academy of-Sciences, vol. 102, No. 37.

Basemen C. et al.: "Light-induced heat production correlated with fluorescence and its quenching mechanism", Photosynthesis Research, vol. 21, No. 2.

Edward Shore and Alex Small: "Optimal Localizing Acquisition scheme for subwavelength localization microscopy of bleachable fluorophores", Optics Letter, vol. 36, No. 2.

Brakemann, Tanja et al.: "A reversibly photoswitchable GFP-like protein with fluorescence excitation decoupled from switching", Nature Biotechnology, vol. 29, No. 10.

* cited by examiner (a)  (b)

(c)  (d)

METHOD OF SPATIAL HIGH RESOLUTION IMAGING OF A STRUCTURE OF A SAMPLE, THE STRUCTURE COMPRISING A LUMINOPHORE

CROSS REFERENCE TO RELATED APPLICATIONS

The present invention is a continuation of International Patent Application PCT/EP2014/050270 filed on Jan. 9, 2014, entitled "Method for spatially high-resolved imaging of a structure of a sample that has a luminophore" and claiming priority to German Patent Application DE 10 2013 100 174.2, filed Jan. 9, 2013, entitled "Verfahren zum räumlich hochauflösenden Abbilden einer einen Luminophor aufweisenden Struktur einer Probe".

FIELD OF THE INVENTION

The invention relates to a method of spatial high resolution imaging of a structure of a sample, the sample comprising a luminophore. More particular, the invention relates to a method of spatial high resolution imaging of a structure of a sample, the structure comprising a luminophore, wherein the sample, in a measurement area, is subjected to an intensity distribution of luminescence inhibiting light comprising a local minimum; wherein the sample, in the measurement area, is subjected to luminescence excitation light which excites the luminophore out of an electronic ground state into a luminescent state; wherein luminescence light emitted out of the measurement area is registered; and wherein the registered luminescence light is assigned to the position of the local minimum within the sample.

BACKGROUND

In a method of spatial high resolution imaging of a structure of a sample, the structure comprising a luminophore, which is known as GSD (Ground State Depletion) scanning fluorescence light microscopy, the luminophore, by means of GSD light comprising a local minimum, via its excited electronic luminescent state, like, for example, via its excited electronic singlet state, is transferred into a dark state, like, for example, into a long living triplet ground state, out of which it is not excited into the luminescent state by luminescence excitation light. Everywhere outside the local minimum of the intensity distribution of the luminescence inhibiting light, this transfer is saturated. I.e. only in the local minimum of the intensity distribution of the luminescence inhibiting light, the luminophore, after subjection to the luminescence inhibiting light, is still in its electronic ground state out of which it is excited into the luminescent state by means of the luminescence excitation light. Luminescence light emitted by the luminophore after excitation by the luminescence excitation light thus exclusively stems from the local minimum of the intensity distribution of the luminescence inhibiting light and may thus be assigned to the position of the local minimum within the sample.

In the method known as GSD, there is a considerable danger of bleaching the luminophore, because the luminophore, both in its long living dark state into which it is transferred by the luminescence inhibiting light, and in the excited electronic luminescent state in which it is temporarily during its transfer into its dark state, to an increased extent tends to chemical reactions, like, for example, with oxygen, and/or is prone to the danger that it is further electronically excited by the luminescence inhibiting light or the luminescence excitation light so that photochemical bleaching of the luminophore occurs.

A further method of spatial high resolution imaging of a structure of a sample, the structure comprising a luminophore, which is known as a variant of RESOLFT (Reversible Saturable Optical Fluorescence Transitions) scanning fluorescence light microscopy, makes use of so-called switchable luminophores. These luminophores, by means of luminescence inhibiting light in the form of switching off light, are switchable out of a first conformation state, i.e. a first atomic configuration, in which they are active as luminophores into a second conformation state in which they are not active as luminophores, i.e. in which they are, at least by means of the luminescence excitation light which, in the first conformation state is suitable for exciting the luminescent state, not excitable into a luminescent state in which they emit the luminescence light registered as the measurement signal. With a sufficient long lifetime of the second conformation state, only comparatively low light intensity distributions are necessary to saturate such a switching process everywhere outside the local minimum of the intensity distribution of the luminescence inhibiting light. Further, there is no significant danger that the luminophore transferred into its other conformation state bleaches out of this other conformation state, as the luminophore does not respond to the luminescence inhibiting light and the luminescence excitation light in this conformation state. However, the transfer of the switchable luminophore into its second conformation state by means of the luminescence inhibiting light also takes place via an excited electronic state which, with high intensities of the luminescence inhibiting light, may be a starting point for photochemical bleaching of the luminophore. For this and other reasons, the absolute number of usable switching processes between the two conformations states are limited with a plurality of switchable luminophores, particularly if they are switched actively, i.e. by means of luminescence enabling light, out of their second not luminescence-able conformation state into their first luminescence-capable conformation state. Further, the already mentioned long lifetimes of the conformation states, even if one actively switches back and forth between the conformation states, mean that the methods of spatial high resolution imaging of a structure of a sample, the structure comprising a luminophore, which are known as RESOLFT, are comparatively slow. Finally, the number of commercially available switchable luminophores which are suitable for marking structures of a sample is limited, particularly, when compared to the high number of generally available luminophores. The development of new stable switchable luminophores is also laborious.

In a method of spatial high resolution imaging of a structure of a sample, the sample comprising a luminophore, which is known as STED (Stimulated Emission Depletion) scanning fluorescence light microscopy, the sample, in a measurement area, is at first subjected to luminescence excitation light which excites the luminophore out of an electronic ground state into a luminescent state. Then, the sample, in the measurement area, is subjected to an intensity distribution of STED light comprising a local minimum, which de-excites the excited luminescent state by stimulated emission back into the ground state. If the luminescence inhibiting light has de-excited the luminescent state everywhere outside the minimum by stimulated emission, luminescence light emitted out of the measurement area afterwards may only stem out of the local minimum of the intensity distribution of the luminescence inhibiting light and may thus be assigned to the position of the local minimum within the sample.

In the method known as STED, a very high spatial resolution in imaging a structure of a sample, the structure comprising a luminophore, is actually achieved. Here, however, the luminophore is considerably stressed photochemically and thus tends to bleach. The reason is that the luminescence inhibiting light which has to be applied at a high absolute intensity for narrowing down the local minimum in the form of a zero point of its intensity distribution acts upon the luminophore already being in its excited luminescent state. Thus, besides the desired stimulated emission which transfers the luminophore back into its ground state, other processes, particularly farther reaching electronic excitations resulting into bleaching of the luminophore, are not unlikely. Even a new excitation of the luminophore at first de-excited by stimulated emission may occur due to the light originally provided for luminescence inhibition.

All known methods of spatial high resolution imaging of a structure of a sample, the structure comprising a luminophore, are based on the fact that the luminescence inhibiting light transfers the luminophore either out of its luminescent-capable ground state via an excited electronic state into a dark state prior to application of the luminescence excitation light, or out of the excited luminescent state back into the ground state. Thus, in each case, the luminophore is subjected to luminescence inhibiting light of high intensity that has a wavelength in the absorption spectrum of the luminophore, and an excited electronic state which is associated with the danger of photochemical bleaching of the luminophore is involved in enhancing the spatial resolution by means of the luminescence inhibiting light. Further, there seems to be a correlation between the lifetime of the dark state and the necessary intensity of the luminescence inhibiting light which may be the lower the longer the lifetime of the dark state.

There still is a need of a method of spatial high resolution imaging of a structure of a sample, the structure comprising a luminophore, in which the luminophore is subjected to a particularly low danger of photochemical bleaching and which nevertheless allows for high velocities in scanning the sample with the minimum of the intensity distribution of the luminescence inhibiting light.

SUMMARY OF THE INVENTION

In one aspect, the present invention relates to a method of high spatial resolution imaging of a structure of a sample, the structure comprising a luminophore having an electronic ground state and a luminescent state into which the luminophore, out of its electronic ground state, is excitable by luminescence excitation light. In a measurement area, the method comprises subjecting the sample to an intensity distribution of luminescence inhibiting light comprising a local minimum, wherein the luminescence inhibiting light is configured to disturb the electronic ground state of the luminophore to such an extent that the luminophore, in its disturbed electronic ground state, has an absorption cross-section for the luminescence excitation light which is reduced by at least 50% as compared to an absorption cross-section for the luminescence excitation light of the luminophore in its undisturbed electronic ground state; and subjecting the sample to the luminescence excitation light exciting the luminophore out of its undisturbed electronic ground state into its luminescent state. Luminescence light emitted out of the measurement area is registered and assigned to a position of the local minimum within the sample.

In another aspect, the present invention relates to another method of high spatial resolution imaging of a structure of a sample, the structure comprising a luminophore having an electronic ground state and a luminescent state into which the luminophore, out of its electronic ground state, is excitable by luminescence excitation light. This method, in addition to the above steps of subjecting, registering and assigning, comprises scanning the sample with the local minimum of the intensity distribution of the luminescence inhibiting light; and repeating the above steps of subjecting registering and assigning for a plurality of positions of the local minimum of the intensity distribution of the luminescence inhibiting light within the sample.

In the method according to the invention, the intensity of the luminescence light emitted out of the measurement area is a measure of the concentration of the luminophore at the position of the local minimum within the sample. By scanning the sample with the local minimum, while repeating the above mentioned steps for each position of the local minimum, the distribution of the luminophore in the sample is determined, and, thus, the structure marked with the luminophore is imaged.

Here, the term "luminophore" designates any substance from which luminescence light may be obtained as a measurement signal, if it is in an excited luminescent state. This definition particularly applies to fluorescence dyes. The process on which the emission of the luminescence light is based, however, does not need to be fluorescence. It may also be scattering, like for example Raman scattering, in which the excited transitional states out of which the scattered light is emitted are regarded as the excited luminescent states here.

The structure of interest of the sample may comprise the luminophore as such, i.e. it may be autoluminescent. The structure of interest of the sample, however, may also be artificially marked with the luminophore. This artificial marking of the structure with the luminophore may, for example, be executed by so-called antibody dyeing, i.e. by coupling the luminophore via an immunoreaction, or by means of genetic engineering resulting in a simultaneous expression of the luminophore and the structure of interest.

If a state, like for example an excitable electronic ground state or an excited luminescent state of the luminophore, is mentioned here, this is an electronic state of the smallest entity of the luminophore capable of luminescence, i.e. of a molecule, of a complex, of a void, of a quantum dot or the like.

If a local minimum of an intensity distribution of light, like for example the luminescence de-excitation light, is mentioned here, this particularly means a zero point of the intensity distribution created by interference. It may be a true zero point in which the intensity of the light in fact goes down to zero, or a zero point in which the intensity of the light in the absence of ideal optical conditions only essentially goes down to zero. If dimensions of a local minimum are mentioned here, these dimensions particularly relate to the dimensions of the volume in which the respective light does not saturate the effect strived for by the respective light, like for example the transfer excited by the respective light.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
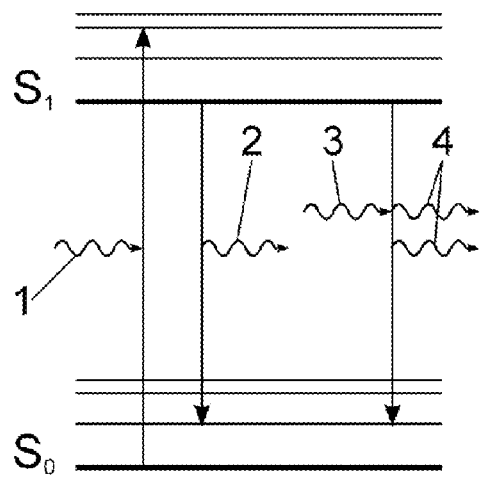
FIG. 1 shows an energy spectrum of a fluorescence dye as an example of a luminophore in its singlet state.

In a method of spatial high resolution imaging of a structure of a sample, the structure comprising a luminophore, wherein the sample, in a measurement area, is subjected to an intensity distribution of luminescence inhibiting light comprising a local minimum, wherein the sample, in the measurement area, is subjected to luminescence excitation light which excites the luminophore out of an electronic ground state into a luminescent state, wherein luminescence light emitted out of the measurement area is registered, and wherein the registered luminescence light is assigned to the position of the local minimum in the sample, the electronic ground state of the luminophore is disturbed by the luminescence inhibiting light such that the luminophore, in the disturbed electronic ground state, has an absorption cross-section for the luminescence excitation light which is reduced by at least 50%. The standard of comparison in assessing the absorption cross-section for the luminescence excitation light is the undisturbed electronic ground state in which the luminophore has 100% of its absorption cross-section for the luminescence excitation light.

In the method according to the invention, the luminophore, by means of the luminescence inhibiting light, is not transferred out of the electronic ground state or out of any other electronic state back into the electronic ground state. I.e. there is no change in the electronic state of the luminophore. Instead, the present electronic ground state of the luminophore is disturbed. This disturbance is at least driven to such an extent that the luminophore in the disturbed electronic ground state, by means of the luminescence excitation light, is only excited into the luminescent state at half the probability at maximum as compared to the undisturbed electronic ground state. Typically, however, the disturbance is driven further so that the absorption cross-section is reduced to 20%, 10%, 5%, 3%, 1% or even less of its starting value in the undisturbed electronic ground state. The disturbance typically relates to the steric configuration of the luminophore, particularly of its atomic nuclei, in its ground state. This steric configuration has an influence on the antenna function of the luminophore for the luminescence excitation light, or, in other words, on the capability of the luminophore for interacting with or, even more particular, for absorbing light, particularly luminescence excitation light. For this reason, the disturbance of the configuration varies the absorption cross-section for the luminescence excitation light.

The effect of the disturbance of the ground state of the luminophore inhibiting the excitation of the luminophore by the luminescence excitation light may be explained according to the Franck-Condon-principle, neglecting that the assumptions on which this principle is based, like, particularly the Born-Oppenheimer-approximation, may be violated with a disturbance affecting both the configuration of the atomic nuclei and the electron cloud. According to the point of view of the Franck-Condon-principle, the disturbed ground state lacks a fitting vibrational sub-state of the luminescent excited electronic state of the luminophore. The Franck-Condon-factors for all vibrational sub-states of the luminescent excited electronic states are thus only small and result in only small transition probabilities. This is equivalent to the absorption cross-section for the luminescence excitation light being reduced according to the invention.

The perception of the disturbed ground state of the luminophore further implies that the disturbed ground state is no state of thermal equilibrium of the luminophore with regard to its surroundings. The disturbance comes along with an increased energy of the luminophore; the disturbance may even transfer the luminophore into a higher vibrational sub-state of its ground state. The increased energy of the luminophore in the disturbed ground state, however, does not correspond to a common increase of temperature of the sample in the surroundings of the luminophore. Instead, the energy of the disturbed ground state is clearly above the thermal energy of the luminophore defined by the temperature in its surroundings. Correspondingly, the disturbance of the electronic ground state of the luminophore caused by the luminescence inhibiting light according to the present invention gets lost as soon as a thermal equilibrium of the luminophore with regard to its surroundings is reached again. Only a small increase of the temperature of the sample remains in the area over which the energy of the disturbance is spread. This means that the timescale which has to be considered in executing the method according to the invention primarily is set by the relaxation time at which the luminophore reaches its thermal equilibrium with its surroundings again. This relaxation time is here also designated as collisional or vibrational relaxation time, as the thermal equilibrium is typically reached by transferring impulses and/or vibrations onto neighboring molecules. The typical order of magnitude of the collisional or vibrational relaxation time is in the higher femtosecond (fs) range up to the picosecond (ps) range, i.e. from a few ten femtoseconds to some picoseconds. Typically, it is in the range of a few hundred up to some hundred femtoseconds.

The period of time in which an increase of the temperature of the sample due to the energy introduced by the luminescence inhibiting light is spread out to such an extent that it also encompasses the local minimum left out by the intensity distribution of the luminescence inhibiting light is by some orders of magnitude longer and in the nanosecond (ns) range up to the microsecond (µs) range. This period of time thus does not set a further relevant time limit in the method according to the invention, particularly, as in this method, even outside the local minimum of the intensity distribution, no general increase of temperature of the sample within the measurement area is intended but is kept as small as possible.

It is to be understood that, in the method according to the invention, the luminescence inhibiting light has a wavelength outside a luminescence excitation spectrum and, in a preferred embodiment, also outside the luminescence de-excitation spectrum of the luminophore such that the luminescence inhibiting light may be selectively employed for disturbing the electronic ground state of the luminophore. Here, a wavelength is regarded as being outside the luminescence excitation spectrum or the luminescence de-excitation spectrum of the luminophore, if the corresponding absorption cross-section is, for example, 5% of the maximum absorption cross-section for the luminescence excitation or de-excitation within the luminescence excitation spectrum or the luminescence de-excitation spectrum at maximum.

The disturbance of the electronic ground state of the luminophore typically occurs via molecular transfer of impulses or vibrations, by, for example, molecular collisions. By means of the impulses or vibrations transferred to the luminophore, its steric configuration is disturbed. The disturbance of the steric configuration here primarily relates to the spatial arrangement of the atomic nuclei of the luminophore, but it will be also accompanied by a disturbance of the electron cloud surrounding the atomic nuclei.

Impulses or vibrations for disturbing the ground state of the luminophore may particularly stem from collisional or vibrational relaxations of at least one modulator entity excited by the luminescence inhibiting light. I.e. the luminescence inhibiting light excites the at least one modulator entity, like, for example, out of its electronic ground state into an excited electronic state which then, by means of collisional or vibrational relaxation, i.e. with transferring impulses and/or vibrations onto the luminophore, returns back into the electronic ground state.

The at least one modulator entity may particularly be a separate molecule or a functional group. Thus, the modulator entity may be selected from the group of non-luminescent dyes, which includes azo dyes, carotenes, cyanics, coumarin derivatives and so-called photosensitizers. Particularly, it may be crystal violet or methylene blue. The luminophore may be a structurally related luminescent dye.

For an efficient transfer of impulses and/or vibrations onto the luminophore, the modulator entity is to be allocated to the luminophore as directly as possible. Thus, for example, the water molecules which are located next to the luminescent center within the hull (barrel) of a green fluorescent protein (GFP) may be used as modulator entities as they are closely neighboring the luminescent center.

Further, it is possible to couple the at least one modulator entity to the luminophore via a bond. Such a bond may be covalent or include a chemical bond. Depending on the kind of bond, the modulator entity is more flexibly or more rigidly coupled to the luminophore. It is essential that, as a result of the collisional or vibrational relaxation of the modulator entity, sufficient kinetic energy for the desired disturbance of the electronic ground state of the luminophore is transferred onto the luminophore.

The modulator entity may be bent with regard to the luminophore to which it is coupled. I.e. it preferably comprises a π-conjugated electron system that is about orthogonal to the π-conjugated electron system of the luminophore. Then, the modulator entity, despite its coupling to the luminophore usable for the transfer of impulses and/or vibrations, does only disturb the luminescence properties of the undisturbed luminophore as little as possible.

Particularly, the modulator entity, by means of the luminescence inhibiting light, may be excited for a cis-trans-isomerization. The rearrangement of an atomic group of the modulator entity taking place during the isomerization is particularly effectively transferred as an impulse onto the couples luminophore, if the luminophore is bonded to the atomic group of the modulator entity being rearranged. One luminophore each may also be coupled to two atomic groups of the modulator entity, whose relative configuration is changed in the isomerization. If the isomerization excited by the luminescence inhibiting light is non-stable and the modulator entity spontaneously returns into its pre-isomerization starting state, a further impulse is transferred to any bonded luminophore, which disturbs the ground state of the respective luminophore.

In the disturbed electronic ground state, particularly an atomic order, i.e. the spatial or steric configuration of atomic nuclei in the luminophore, is disturbed. Here, the disturbance may also be a vibration of the atoms in the direction towards any other, not luminescence-capable conformation state of the luminophore, wherein this other conformation state, however, is either not reached or not stable. In any case, the already mentioned capability of the luminophore of interacting with the luminescence excitation light is purposefully affected by the disturbance. As also already mentioned, such a disturbance, even if it has effectively been excited, is only of a short duration, as it does not correspond to any thermal equilibrium of the luminophore. Correspondingly, the method steps of the method according to the invention, as compared to known methods of spatially high resolution imaging of a sample, have to be executed quickly following to each other.

Particularly, the sample should only be subjected to a pulse of the luminescence excitation light in the measurement area, when the electronic ground state of the luminophore is disturbed by a pulse of the luminescence inhibiting light. I.e. the luminescence excitation light should neither be applied to the sample prior to the disturbance of the ground state of the luminophore nor after fading away of this disturbance. As a consequence, the luminescence excitation light, outside the minimum of the intensity distribution of the luminescence inhibiting light, essentially encounters luminophore with a disturbed ground state so that, outside the minimum, there is no relevant excitation of the luminescent state. If this condition is met, the luminescence light which is registered from the sample may only stem from the local minimum of the intensity distribution of the luminescence inhibiting light, independently of whether it is registered during or after subjecting the sample with the luminescence excitation light.

For the purpose of in fact having the desired spatial distribution of the disturbance of the ground state when applying the luminescence excitation light, the luminophore, out of its disturbed ground state, may not yet have reached a thermal equilibrium with its surroundings again. Periods of 1000 fs, 500 fs or even smaller for a maximum distance in time of the luminescence excitation light from the luminescence inhibiting light may have to be kept to ensure this. If it is not possible or if it would only be possible at high efforts to limit the luminescence excitation light to a period in which the electronic ground state of the luminophore is in fact disturbed, the resolution enhancing effect of the method according to the invention may be optimally used in that a period of time in which the luminescence light emitted out of the measurement area is already terminated while the electronic ground state of the luminophore is still disturbed by a previous pulse of the luminescence inhibiting light, even if the pulse of the luminescence excitation light is not yet over. Such a "gating" of the detected luminescence light with temporal resolution in the order of the collisional or vibrational relaxation time of the disturbed ground state allows for registering luminescence light from such luminophore which has been excited at a point in time at which the disturbance of the electronic ground state of the luminophore has been present at the desired spatial distribution about the minimum of the intensity distribution of the luminescence inhibiting light. Typically, the limited period of time in which the emitted luminescence light is registered in the method according to the invention while a continued excitation of the luminophore by means of the luminescence excitation light takes place, terminates not more than a few ps, often only about 1 ps after the pulse of the luminescence inhibiting light.

As compared to the typical lifetime of fluorescent states, a few ps may only be short and thus not be sufficient to detect higher percentages of the luminescence light which would generally be obtainable from the excited luminophore. Other luminescent states including luminescent triplet states electronically excited out of a triplet ground state or luminescent transition states of, for example, Raman-scattering substances involved in the scattering of light, may, however, have much shorter lifetimes. In disturbing the ground state of a light scattering substance by means of the luminescence inhibiting light according to the invention, their scattering spectrum is shifted or otherwise varied.

At a first approximation, the duration of the pulse of the luminescence inhibiting light does not matter, as long as the energy transferred by means of the pulse is sufficient to cause the desired disturbance of the ground state of the luminophore. Generally, the luminescence inhibiting light may thus also be applied continuously. This would, however, be associated with an undesired introduction of heat into the sample which would make it increasingly difficult to locally disturb the electronic ground state of the luminophore only outside the minimum of the intensity distribution of the luminescence inhibiting light. It is a known phenomenon that the fluorescence light emission of fluorescence dyes decreases with increasing temperature. A general increase of the temperature of the sample would also reduce its absorption cross-section in its undisturbed ground state, i.e. in its ground state in thermal equilibrium. Thus, in the present invention, it is preferred to apply the luminescence inhibiting light in short pulses which are typically between 10 fs and 1000 fs, often between 50 fs and 500 fs long and which may particularly be 300 fs long. With such short pulses, only a limited energy is transferred to the sample which may also be dissipated while scanning the sample without a general increase of the temperature of the sample. The energy to be transferred into the measurement area of dimensions defined by the diffraction barrier for a disturbance of the ground state of the luminophore according to the invention is in a typical range of 1 pJ to 10,000 pJ and often between 5 pJ and 500 pJ per pulse of the luminescence inhibiting light. With this energy, the resulting increase of the temperature of the sample in the measurement area remains small, even if the energy introduced by the luminescence inhibiting light is not removed from the sample.

Preferably, the pulse of the luminescence inhibiting light has such an intensity that it saturates a disturbance of the electronic ground state of the luminophore in the measurement area outside the local minimum of its intensity distribution. I.e., the disturbance of the electronic ground state in the measurement area, everywhere outside the local minimum, is at least so high that the absorption cross-section for the luminescence excitation light is reduced by at least 50%.

Practically, the pulse of the luminescence inhibiting light may be dimensioned so that it saturates an excited state of the at least one modulator entity relaxing by collisional or vibrational relaxation. By providing the modulator entity in a sufficient density, the desired disturbance of the desired ground state of the luminophore may then be ensured everywhere outside the minimum of the intensity distribution of the luminescence inhibiting light.

The method according to the invention, at a minimum effort, allows for simultaneously imaging different structures which comprise different luminophores, i.e. luminophores emitting luminescence light of different wavelengths. For this purpose, it is generally sufficient that same modulator entities which are all excitable by the same excitation inhibiting light are coupled to the various luminophores, and that the luminescence light of the different wavelengths is registered separately and assigned to the individual luminophores at the position of the local minimum of the intensity distribution of the excitation inhibiting light. The local minimum of the intensity distribution of the excitation inhibiting light defines the volume of the sample out of which the luminescence light may stem for all luminophores to which the modulator entities are coupled. Even if the excitation of the various luminophores into their luminescent states takes place by luminescence excitation light of different wavelengths adjusted to the respective luminophore, this is no problem because no local minimum of different intensity distributions have to be brought to coincidence as it is often required in simultaneous imaging of different structures comprising different luminophores.

In another further developed embodiment of the method according to the invention, the sample, prior to registering the luminescence light emitted out of the measurement area, is additionally subjected to an intensity distribution of conventional luminescence inhibiting light comprising a local minimum, which falls into the absorption spectrum of the luminophore and which inhibits luminescence of the luminophore involving an excited electronic state. The additional conventional luminescence inhibiting light may further narrow down the spatial area out of which the luminescence light may be emitted out of the sample according to the known STED, GSD or RESOLFT principle. I.e. the conventional luminescence inhibiting light may be STED, GSD or switch off light, the latter requiring a switchable luminophore. However, there is no or at least a considerably smaller danger of bleaching the luminophore here, as the typical danger of bleaching the luminophore in STED, GSD or RESOLFT, as the high intensities of the conventional luminescence inhibiting light only (or at least mainly) act upon luminophore which is in its disturbed ground state but not in a state electronically excited and thus tending to photochemical bleaching. In this embodiment of the method according to the invention, the conventional luminescence inhibiting light is effective at the comparatively low intensities close to the local minimum of the intensity distribution which are not associated with a higher danger of photochemically bleaching the luminophore.

The variant of the method according to the invention described at last may also be interpreted such that due to the disturbance of the ground state by means of the luminescence inhibiting light, the luminophore in the area of the high intensities of the STED, GSD or switch off light in an STED, GSD or RESOLFT method is transferred into a protection state in which it is not so prone to the danger of being photochemically bleached by the high intensities of the STED, GSD or switch off light as otherwise. This advantageous effect is generally also achieved, if the luminescence inhibiting light according to the invention primarily disturbs the ground state of the luminophore without electronic excitation of this ground state, but is partially also effective as conventional luminescence inhibiting light, i.e. as STED, GSD or switch off light, and thus in two ways but at one wavelength increases the spatial resolution of the method according to the invention.

Now referring in greater detail to the drawings, the energy spectrum of a fluorescence dye in its singlet state illustrated in FIG. 1 includes an electronic ground state $S_0$ with different vibrational sub-states, and a luminescent excited electronic state $S_1$. By means of excitation light 1, the fluorescence dye can be excited out of its ground state $S_0$ into its excited state $S_1$. This state $S_1$ spontaneously decays into the ground state $S_0$ with luminescence light 2, here particularly fluorescence light, being emitted. Already prior to the emission of the luminescence light 2, the excited state $S_1$ may, however, purposefully be depleted by means of STED light 3, which has a different wavelength than the excitation light 1 and the luminescence light 2 and which returns the fluorescence dye out of its excited state $S_1$ into its ground state $S_0$ via stimulated emission of light 4 of the same wavelength as the STED light. The excitation light 1 may have another wavelength than the luminescence light 2, particularly a shorter wavelength, as well so that the luminescence light 2 may be separated from all other light by its wavelength.

The absorption cross-section at which the excitation light 1 is absorbed, i.e. the probability that the excitation light 1 results in excitation of the fluorescence dye out of its ground state $S_0$ into its excited electronic state $S_1$ depends on whether the fluorescence dye is in a low energy vibrational sub-state of the ground state $S_0$. Thus, the absorption cross-section decreases with a strong increase of the temperature of the fluorescence dye and thus with the population of higher vibrational sub-states of the ground state $S_0$. In the method according to the invention, however, no general increase of temperature of the fluorescence dye in thermal equilibrium is caused. Instead, the fluorescence dye, outside a minimum of an intensity distribution of fluorescence or luminescence inhibiting light, is disturbed by one or more impulses and/or a direct transfer of vibrations such that is remains in its electronic ground state $S_0$ but that the absorption cross-section for the excitation light 1 is considerably reduced. This may be interpreted as an increase of the vibration or oscillation energy of the individual fluorescent dye by the respective collision and a corresponding reduction of the absorption cross-section for the excitation light 1. This increase in energy clearly exceeds the thermal energy of the fluorescence dye due to the temperature of its surroundings. If, in the method according to the invention, after terminating the subjection to the luminescence inhibiting light, a thermal equilibrium of the fluorescence dye with its surroundings is reached again, the disturbance of its ground state, which reduces the absorption cross-section for the excitation light 1, is already lost again. For a certain period of time, a remaining small increase of temperature of the fluorescence dye in thermal equilibrium with its surroundings may still have a local minimum at the position of the local minimum of the intensity distribution of the luminescence inhibiting light but does no longer result in significantly different absorption cross-sections for the luminescence excitation light within and outside of the local minimum. Only the thermal non-equilibrium state directly after the collisional excitation of the fluorescence dye can be used for increasing the spatial resolution.

Figure 2:
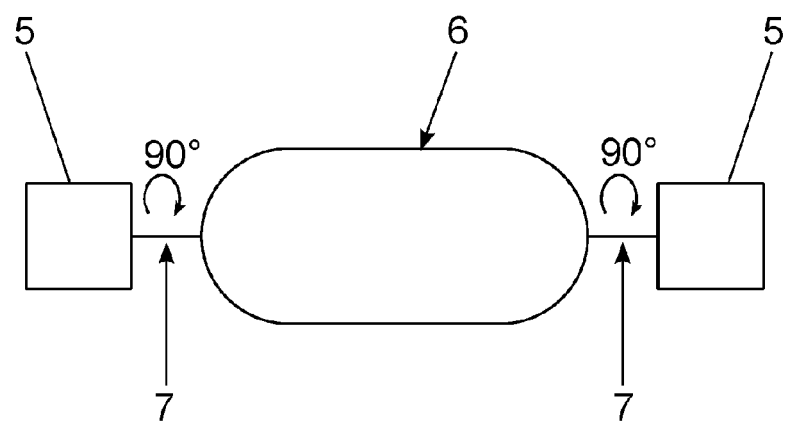
FIG. 2 schematically shows a luminophore with two coupled modulator entities.

Modulator entities 5 may be coupled to the luminophore 6, which absorb the luminescence inhibiting light and transform it into impulses and/or oscillations, to cause this collisional excitation of a luminophore, for which the fluorescence dye described up to now is an example. This is sketched in FIG. 2, where two modulator entities 5 are coupled to the luminophore 6 via bonds 7 at angles of 90° so that their π-conjugated electron systems are essentially orthogonal to that one of the luminophore 6. The number of the modulator entities 5 may also be lower or higher than two. The kind of the bond may also vary. Bonds which do not affect the luminescent properties of the luminophore 6 but effectively transfer an impulse and/or vibrations coming from the modulator entities 5 onto the luminophore 6 are ideal. Particularly, compounds which are excitable for a cis-trans-isomerization by means of the luminescence inhibiting light, like, for example, azo-chromophores, are well suited as modulator entities 5 to transfer such impulses onto each coupled luminophore 6 which disturb its ground state according to the invention. Here, two luminophores may be coupled to the two atomic groups of the modulator entity which are rearranged relative to each other in the isomerization.

Figure 3:
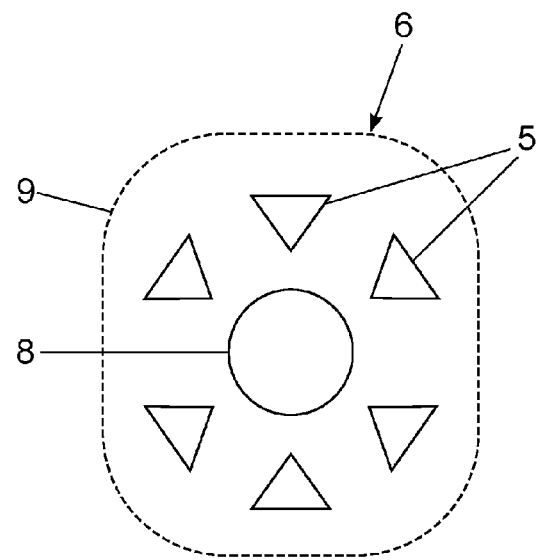
FIG. 3 schematically illustrates a luminophore in which several modulator entities together with a luminescent center are arranged within a common hull.

FIG. 3 shows a luminophore 6 in which a luminescent center 8 together with modulator entities 5 is tightly enclosed by a hull 9. Such a constellation is, for example, present with the green fluorescent protein, where the modulator entities 5 are water molecules. These water molecules may be excited by means of luminescence inhibiting light into a state which decays by vibrational or collisional relaxation, with the impulses and oscillations coming from the modulator entities 5 being transferred onto the luminophore 6 or its luminescent center 8 and reduce its absorption cross-section for the excitation light 1 according to FIG. 1.

Figure 4:
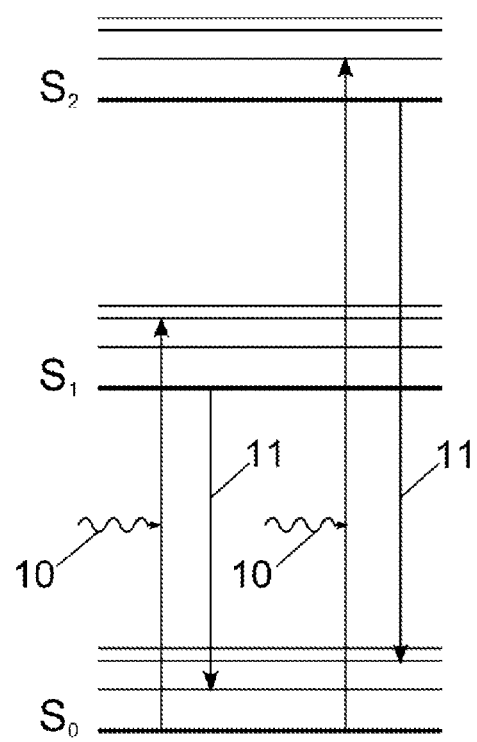
FIG. 4 shows an energy spectrum of a modulator entity in its singlet state.

FIG. 4 illustrates the energy spectrum of a modulator entity 5 in its singlet state. By the luminescence inhibiting light 10, the modulator entity 5 is transferred out of the ground state $S_0$ into an excited electronic state, like for example its $S_1$ or $S_2$ state. The energy needed for exciting the transfer into the higher $S_2$ state may be provided by a wavelength of the excitation light in the UV range and thus outside the absorption and emission spectrum of the luminophore 6. The excited $S_1$ or $S_2$ state very quickly decays back into the ground state $S_0$ by vibrational or collisional relaxation 11, wherein an impulse and/or oscillations are transferred to the luminophore 6 and disturb its ground state in the desired way with a suitable coupling of the modulator entity 5.

Figure 5:
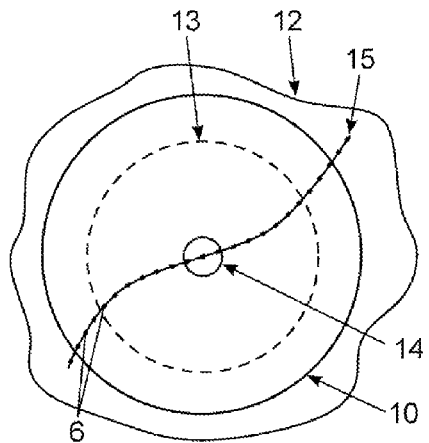
FIG. 5 illustrates the individual steps of a method according to the invention.
Figure 5:
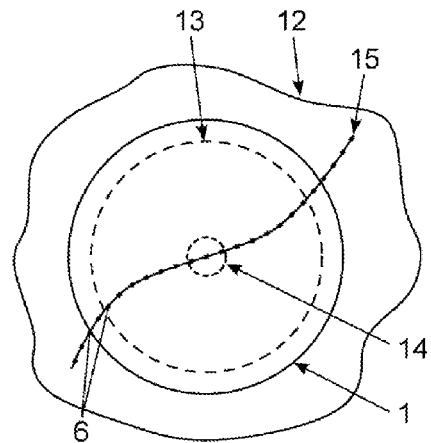
Figure 5:
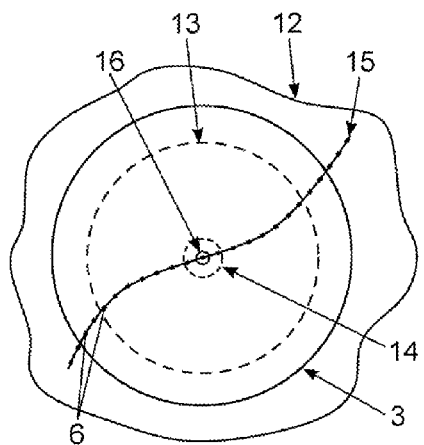
Figure 5:
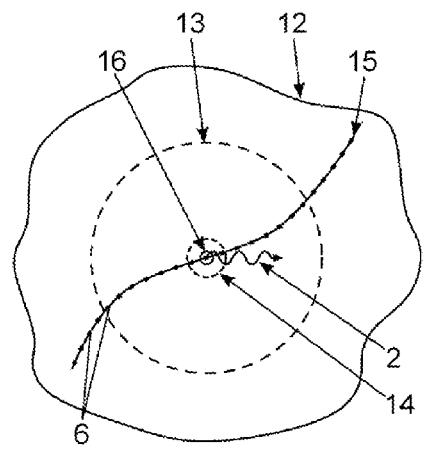

FIG. 5 (*a*) to (*d*) illustrates the steps of the method according to the invention. According to FIG. 5(*a*), a sample 12 in a measurement area 13 is subjected to the luminescence inhibiting light 10. Here, the intensity distribution of the luminescence inhibiting light 10 has a local minimum 14 in the form of a zero point within the center of the measurement area 13. I.e. everywhere outside the local minimum 14, but not within the local minimum 14, the luminescence inhibiting light 10 disturbs the ground state of the luminophore 6 by which a structure 15 in the sample 12 is marked.

In a next step according to FIG. 5(*b*), the sample 12 is subjected to excitation light 1 in the measurement area 13. Only (or at least essentially only) in the local minimum 14 of the luminescence inhibiting light 10, the excitation light 1 can excite the luminophore 6 according to FIG. 1, which, for example, is a fluorescence dye. Thus, luminescence light 2 out of the measurement area 13 registered in a step according to FIG. 5(*d*) may be assigned to the local minimum 14 as it may only (or at least essentially only) stem from the luminophore 6 within this local minimum 14.

In FIG. 5(*c*), an additional optional method step is illustrated in which the sample 12 prior to the step (d), in the measurement area 13, is additionally subjected to STED light 3 which also has a local minimum 16 in the center of the measurement area 13. If this local minimum 16 is even smaller than the local minimum 14, the spatial assignment of the luminescence light 2 according to FIG. 5(*d*) may even be narrowed down further so that the spatial resolution in imaging the structure 15 is increased even further.

The steps illustrated in FIG. 5 are repeated in scanning the sample with the local minimum 14 or 16 for all positions of the local minimum in the sample. In this way, the distribution of the luminophore 6 in the sample is determined and, thus, the structure marked with the luminophore 6 is imaged.

The intensity distributions of the luminescence inhibiting light 10 and of the STED light 3 indicated in FIG. 5 are only exemplary. They may have any other forms, i.e. any intensity courses limiting the local minimum 14 or 16 as they are known from STED fluorescence light microscopy.

Figure 6:
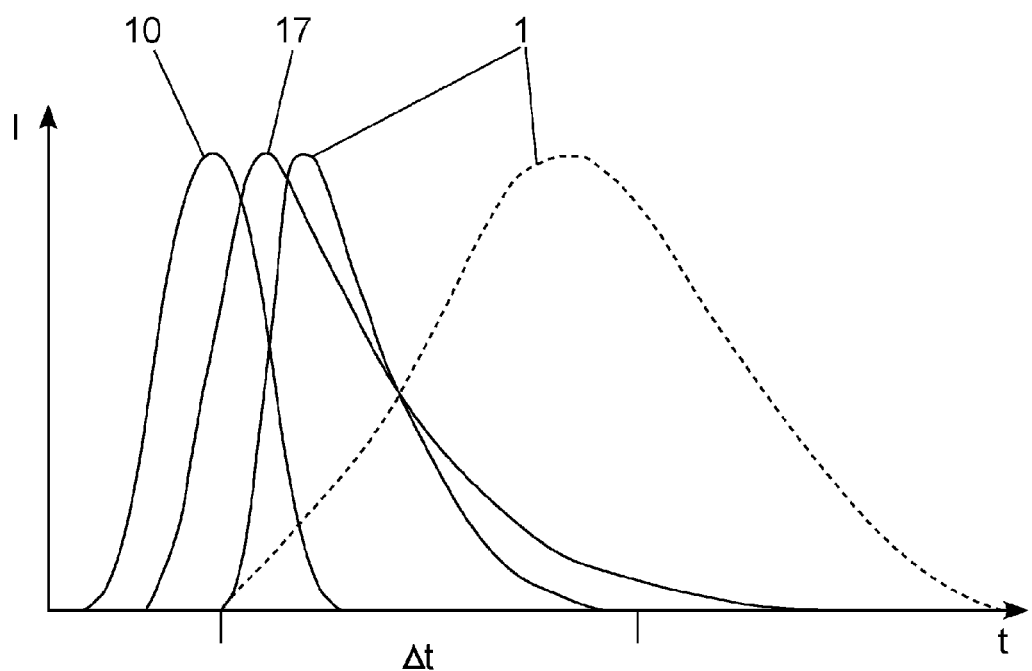
FIG. 6 is a time course diagram of essential steps of the method illustrated in FIG. 5.

FIG. 6 illustrates the temporal sequence of a pulse of the luminescence inhibiting light 10, the resulting disturbance 17 of the ground state of the luminophore, a following pulse of the excitation light 1 and a period of time Δt in which the luminescence light from the sample is registered. Here, with a continuous line, a short pulse of the excitation light 1 is depicted which only begins after the start of the disturbance 17 and already ends prior to the fading away of the disturbance 17. In this case, the period of time Δt may even be extended until the signal-to-noise ratio drops without affecting the spatial resolution. On the other hand, with a dashed line, a longer pulse of the excitation light 1 is depicted which also only starts after the start of the disturbance 17 but which also only ends after the fading away of the disturbance 17. To nevertheless only register the luminescence light from the sample out of the local minimum of the intensity distribution of the luminescence inhibiting light 10, the period of time Δt terminates after a preset time following to the pulse of the luminescence inhibiting light 10. This time is selected such that the disturbance 17 of the ground state of the luminophore has not yet faded away outside of the local minimum 14 according to FIG. 5. The period of time Δt thus typically terminates a few ps, often only about 1 ps, after the pulse of the luminescence inhibiting light 10.

Many variations and modifications may be made to the preferred embodiments of the invention without departing substantially from the spirit and principles of the invention. All such modifications and variations are intended to be included herein within the scope of the present invention, as defined by the following claims.

The invention claimed is:

1. A method of spatial high resolution imaging of a structure of a sample, the structure comprising a luminophore having an electronic ground state and a luminescent state into which the luminophore, out of its electronic ground state, is excitable by luminescence excitation light, the method comprising
   in the measurement area, subjecting the sample to an intensity distribution of luminescence inhibiting light comprising a zero point, wherein the luminescence inhibiting light is configured to disturb the electronic ground state of the luminophore to such an extent that the luminophore, in its disturbed electronic ground state, has an absorption cross-section for the luminescence excitation light which is reduced by at least 50% as compared to an absorption cross-section for the luminescence excitation light of the luminophore in its undisturbed electronic ground state;
   in the measurement area, subjecting the sample to the luminescence excitation light exciting the luminophore out of its undisturbed electronic ground state into its luminescent state;
   registering luminescence light emitted out of the measurement area; and
   assigning the registered luminescence light to a position of the zero point within the sample.

2. The method of claim 1, wherein the luminophore has a luminescence excitation spectrum and a luminescence emission spectrum, and wherein the luminescence inhibiting light has a wavelength outside at least one of the luminescence excitation spectrum and the luminescence emission spectrum of the luminophore.

3. The method of claim 1, wherein the luminescence inhibiting light is configured to disturb the electronic ground state of the luminophore via at least one of molecular impulses and vibrations.

4. The method of claim 3, wherein the luminescence inhibiting light is configured to excite at least one modulator entity for generating the at least one of molecular impulses and vibrations.

5. The method of claim 4, wherein the at least one modulator entity is allocated to the luminophore.

6. The method of claim 4, wherein the at least one modulator entity is chemically bonded to the luminophore.

7. The method of claim 4, wherein the luminescence inhibiting light is configured to excite the modulator entity for a cis-trans-isomerization.

8. The method of claim 1, wherein the luminescence inhibiting light is configured to disturb an atomic order within the luminophore.

9. The method of claim 1, wherein the luminescence inhibiting light is configured to disturb the electronic ground state of the luminophore to such an extent that the luminophore being in the disturbed electronic ground state is not in a thermal equilibrium with its surroundings in the sample.

10. The method of claim 1, wherein the luminescence excitation light is applied to the sample in pulses, and wherein the pulses of the luminescence inhibiting light have a duration in a range from 10 fs to 10,000 fs.

11. The method of claim 10, wherein the pulses of the luminescence inhibiting light have an energy in the measurement area in a range from 1 pJ to 1000 pJ.

12. The method of claim 10, wherein the luminescence inhibiting light is applied to the sample in pulses, and wherein the sample, within the measurement area, is only subjected to a pulse of the luminescence excitation light when the electronic ground state of the luminophore outside the zero point is disturbed by a pulse of the luminescence inhibiting light.

13. The method of claim 10, wherein a period of time in which the luminescence light emitted out of the measurement area is registered is terminated while the electronic ground state of the luminophore is still disturbed by a previous pulse of the luminescence inhibiting light.

14. The method of claim 10, wherein the pulses of the luminescence inhibiting light are configured to, outside the zero point, saturate a disturbance of the electronic ground state of the luminophore within the measurement area.

15. The method of claim 10, wherein the luminescence inhibiting light is configured to excite at least one modulator entity for generating at least one of molecular impulses and vibrations to disturb the electronic ground state of the luminophore via the at least one of molecular impulses and vibrations, wherein each pulse of the luminescence inhibiting light saturates the excitation of the at least one modulator entity.

16. The method of claim 4, wherein same modulator entities are coupled to different luminophores which, out of their luminescent states, emit luminescence light of different wavelengths, and that the luminescence light of the different wavelengths is registered and assigned separately to the individual luminophores at the position of the zero point.

17. The method of claim 1, wherein the sample, prior to registering luminescence light emitted out of the measurement area, is subjected to an intensity distribution of one of conventional STED light, GSD light and switching off light comprising a further zero point overlapping with the zero point of the intensity distribution of the luminescence inhibiting light.

18. A method of spatial high resolution imaging of a structure of a sample, the structure comprising a luminophore having an electronic ground state and a luminescent state into which the luminophore, out of its electronic ground state, is excitable by luminescence excitation light, the method comprising in the measurement area, subjecting the sample to an intensity distribution of luminescence inhibiting light comprising a zero point, wherein the luminescence inhibiting light is configured to disturb the electronic ground state of the luminophore to such an extent that the luminophore, in its disturbed electronic ground state, has an absorption cross-section for the luminescence excitation light which is reduced by at least 50% as compared to an absorption cross-section for the luminescence excitation light of the luminophore its undisturbed electronic ground state;

in the measurement area, subjecting the sample to the luminescence excitation light exciting the luminophore out of its undisturbed electronic ground state into its luminescent state;

registering luminescence light emitted out of the measurement area;

assigning the registered luminescence light to a position of the zero point within the sample;

scanning the sample with the zero point of the intensity distribution of the luminescence inhibiting light; and repeating the steps of subjecting, registering and assigning for a plurality of positions of the zero point of the intensity distribution of the luminescence inhibiting light within the sample.

19. The method of claim 18, wherein the luminophore has a luminescence excitation spectrum and a luminescence emission spectrum, and wherein the luminescence inhibiting light has a wavelength outside at least one of the luminescence excitation spectrum and the luminescence emission spectrum of the luminophore.

20. The method of claim 1, wherein the luminescence excitation light is applied to the sample in pulses, and wherein the pulses of the luminescence inhibiting light have a duration in a range from 50 fs to 500 fs, and an energy in the measurement area in a range from 50 pJ to 500 pJ.

* * * * *